United States Patent [19]

Kennedy et al.

[11] Patent Number: 5,130,231
[45] Date of Patent: Jul. 14, 1992

[54] BLOOD PLASMA TEST DEVICE INCLUDING A SEMIPERMEABLE MEMBRANE MADE OF AN EXPANDED HYDROPHOBIC MATERIAL THAT HAS BEEN TREATED WITH A SURFACTANT

[75] Inventors: Paul R. Kennedy, Warsaw; Ernest C. Adams, North Webster; William E. Woenke, Pierceton, all of Ind.

[73] Assignee: Chem-Elec, Inc., North Webster, Ind.

[21] Appl. No.: 364,893

[22] Filed: Jun. 12, 1989

Related U.S. Application Data

[62] Division of Ser. No. 788,793, Oct. 18, 1985, Pat. No. 4,839,296.

[51] Int. Cl.⁵ .................. C12Q 1/28; C12Q 1/54; C12Q 1/58; G01N 21/78
[52] U.S. Cl. .................................... 435/4; 422/56; 435/10; 435/11; 435/12; 435/14; 435/28; 435/805; 436/170; 436/178
[58] Field of Search ............... 422/56, 57, 58, 66; 436/169, 170, 178; 210/651, 500.36; 435/4, 10–12, 14, 28, 805

[56] References Cited

U.S. PATENT DOCUMENTS

| | | |
|---|---|---|
| 3,092,465 | 6/1963 | Adams et al. |
| 3,368,872 | 2/1968 | Natelson |
| 3,983,005 | 9/1976 | Goodhue et al. |
| 3,992,158 | 11/1976 | Przybylowicz et al. |
| 4,066,403 | 1/1978 | Bruschi |
| 4,144,306 | 3/1979 | Figueras |
| 4,223,089 | 9/1980 | Rothe et al. ............... 435/12 |
| 4,248,924 | 2/1981 | Okita ....................... 428/212 |
| 4,292,272 | 9/1981 | Kitajima et al. ............ 422/57 |
| 4,476,222 | 10/1984 | Ohtani et al. ............. 435/14 |
| 4,477,575 | 10/1984 | Vogel et al. .............. 436/170 |
| 4,501,785 | 2/1985 | Nakanishi ................. 428/195 |
| 4,501,793 | 2/1985 | Sarada .................... 428/315.5 |
| 4,613,441 | 9/1986 | Kohno et al. ............ 210/500.36 |

Primary Examiner—Robert J. Hill, Jr.
Attorney, Agent, or Firm—Roger M. Rickert

[57] ABSTRACT

Single or multiple blood plasma component concentrations are measured by a disposable stick having one or more blood plasma component reactive areas covered by a semipermeable membrane which is permeable by blood plasma or serum components and impermeable by blood cellular and particulate matter. A second overlay may be superposed with the semipermeable membrane over the reactive areas to receive a blood sample and meter and distribute that sample uniformly to the semipermeable membrane which in turn passes the plasma components uniformly to the reactive areas. The overlays are subsequently separable from the reactive area to remove the cellular components and particulate matter and expose the reactive areas for inspection by, for example, color comparison to standardized charts.

12 Claims, 3 Drawing Sheets

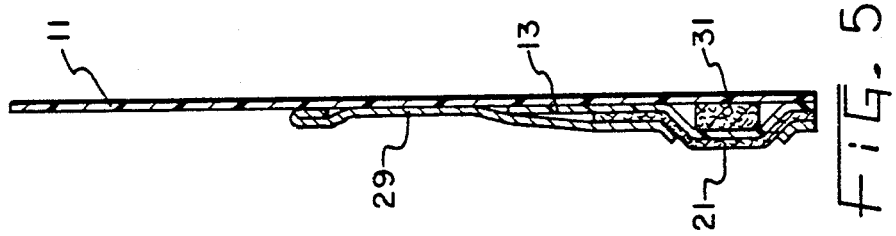
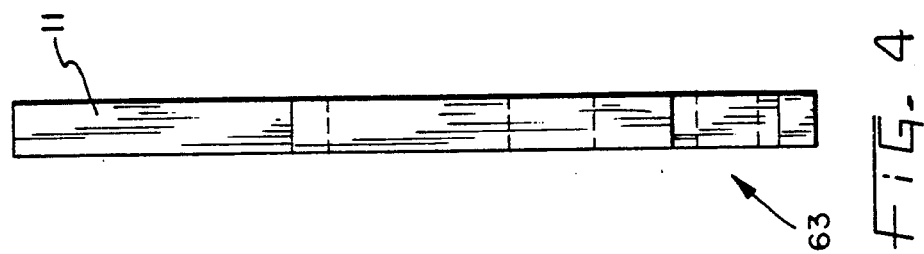
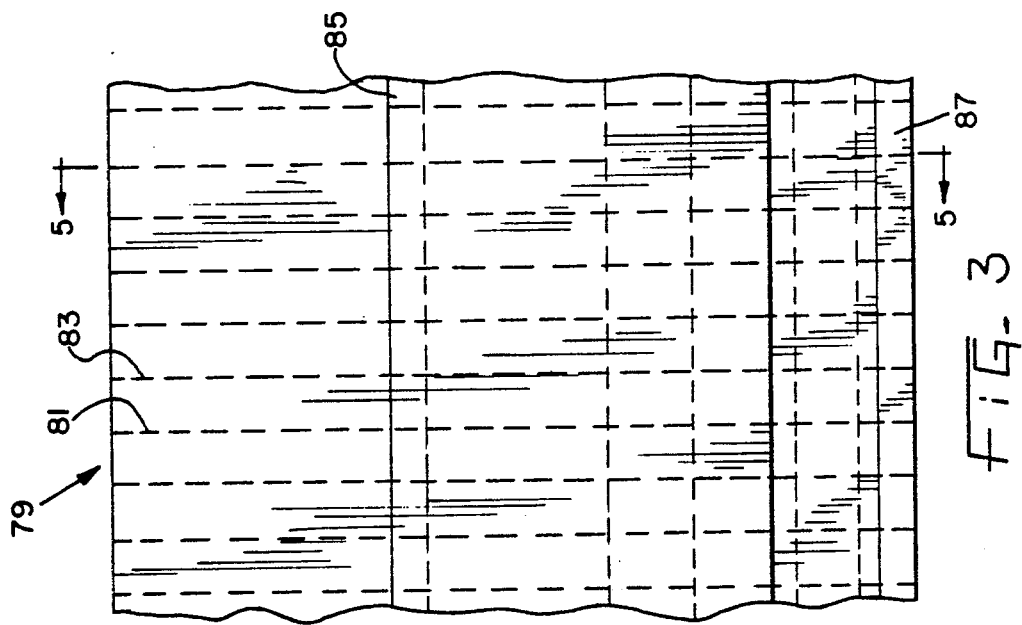
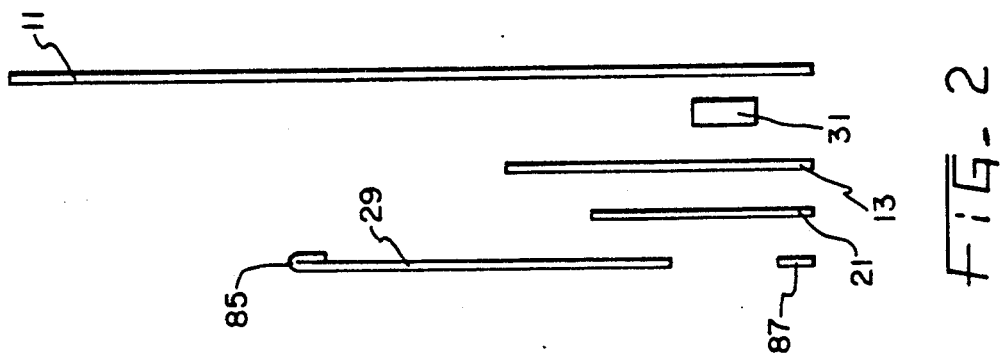

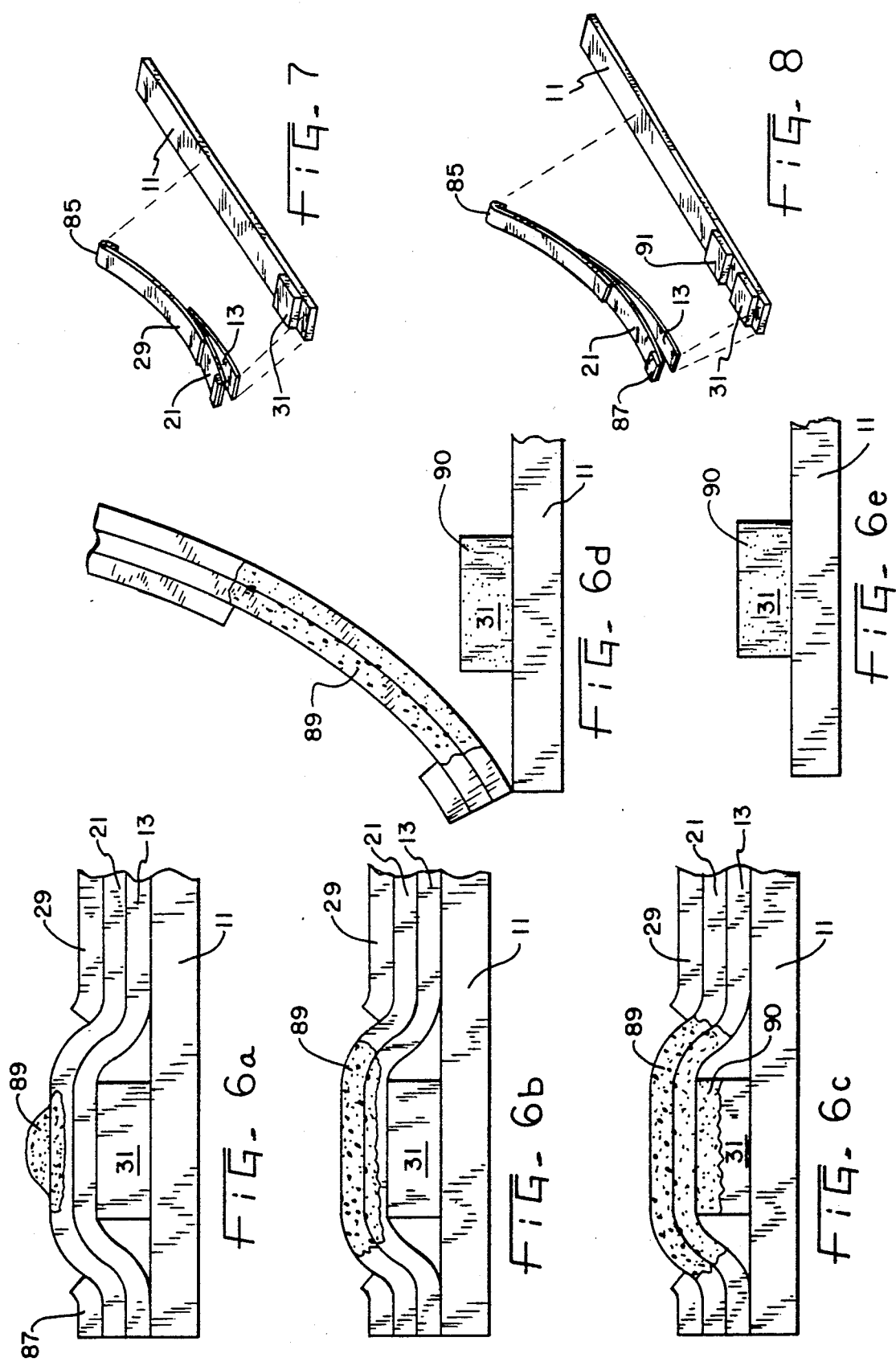

BLOOD PLASMA TEST DEVICE INCLUDING A SEMIPERMEABLE MEMBRANE MADE OF AN EXPANDED HYDROPHOBIC MATERIAL THAT HAS BEEN TREATED WITH A SURFACTANT

This is a divisional application of application Ser. No. 788,793, filed Oct. 18, 1985, now U.S. Pat. No. 4,839,296.

BRIEF SUMMARY OF THE INVENTION

The present invention relates generally to diagnostic devices and techniques and more particularly to arrangements for testing the blood of humans or other animals to determine the concentration of selected plasma components.

Test strips or sticks which are to be immersed in or subjected to a sample and which include an indicator which changes color in response to the presence of a particular substance in the sample are old and well known, including, for example, the familiar litmus or other indicator papers for determining the pH or hydrogen ion concentration of solutions as well as other somewhat more sophisticated test devices for detecting clinically significant substances in biological fluids such as glucose or protein in blood or urine samples.

A rather complete discussion of test strips as to both their chemistry and techniques of manufacture and use may be found in U.S. Pat. Nos. 4,361,648 and 4,362,697, with both patented arrangements suggesting among others the use of 3,3',5,5'tetramethylbenzidine as an indicator material which exhibits a color change in response to an enzyme catalyzed reaction. These commonly owned patented schemes are concerned with testing a wide variety of body fluids for cholesterol, glucose et al and include the suggestion of peroxidase and peroxidase-like substances as catalysts in promoting the color change reaction on the indicator. Many of the techniques disclosed in these patents are limited to laboratory environments.

Test strips or sticks of the general type illustrated in the two aforementioned patents have been used under other than laboratory conditions. For example, U.S. Pat. No. 3,092,465 co-invented by one of the co-inventors herein employs a double enzyme reaction for determining the concentration of glucose in blood. In this patented arrangement which is suitable for individual home use, a drop of blood is placed on a semipermeable membrane and after a specified time interval the surface of that membrane is wiped or washed to remove the cellular and particulate blood components that did not pass through the semipermeable membrane so that the reaction induced by the glucose which did pass through the membrane may be observed through the membrane. Tests employing this patented arrangement yield fairly accurate results, however, the degree of washing or wiping and thus the degree to which the colored blood stains are removed from the membrane, may have a significant effect on the color interpretation of the test results. Further, the blood serum or plasma contacts different portions of the enzyme treated reactive area at different times due to the mechanical distributing of the serum both through the semipermeable membrane and spreading laterally, thus producing color variation within the reactive area. Thus in making the color comparison one is not sure whether the central portion of the reactive area or the periphery should be compared to the standard color chart.

One of the co-inventors herein has recently developed an alcohol concentration test stick in which human saliva is the body fluid sampled. This test stick, as disclosed in co-pending U.S. patent application Ser. No. 703,335, filed Feb. 20, 1985, now U.S. Pat. No. 4,786,596, and assigned to the assignee of the present invention, employs a double enzyme reaction and resulting concentration indicative color change. Some of the manufacturing hardware and techniques in this co-pending application find applicability herein.

Among the several objects of the present invention may be noted the provision of a blood serum test strip of enhanced reliability; the provision of a blood testing strip wherein the cellular and particulate blood components are initially blocked and subsequently stripped away allowing unimpeded visual inspection of a reactive area; the provision of a blood serum testing strip wherein a multiplicity of serum components may be simultaneously concentration tested; the provision of a unique semipermeable membrane arrangement for separating plasma components from whole blood for testing purposes; the provision of a disposable blood component level measuring arrangement with enhanced spreading and metering of the blood sample; and overall improvements in blood component concentration testing techniques.

Also among the several objects of the present invention may be noted the unique physical properties of the removable membranes, enhanced accuracy and reproducibility and capability of further processing.

Membranes described in U.S. Pat. No. 3,092,465 become a permanent part of the reactive pad. The thinness and/or permanence of these membranes do not facilitate removal of the membrane; therefore they must be washed or wiped.

Unlike the above-mentioned membranes, expanded PTFE and the spun bonded polyester, but not necessarily limited to these materials, have the strength to allow them to be pulled away from the reactive pad while retaining the thinness necessary to allow efficient passage of analytes.

Attempting to meet the suggested thoroughness of removal of blood cells by washing or wiping, inaccurate and variable timing is introduced, which leads to inaccurate values as well as poor reproducibility.

The present invention of stripping away the membrane along with cellular and particulate components facilitates an accurate timing and thus leads to more accurate and reproducible values.

This capability of membrane removal allows further processing of the pad with reagents containing molecules which cannot penetrate a semipermeable membrane.

These as well as other objects and advantageous features of the present invention will be in part apparent and in part pointed out hereinafter.

In general a process of testing whole blood for certain plasma component concentrations includes the superimposition of a semipermeable membrane and a blood plasma component reactive area and the subsequent subjecting of the semipermeable membrane to a whole blood sample so that plasma components pass through the membrane and onto the reactive area while cellular and particulate components are blocked by the membrane. Thereafter separation of the membrane from the reactive area allows measurement of the extent of a plasma component induced change in the reactive area.

Also in general and in one form of the invention, a blood component level determination stick has a supporting matrix, a reactive pad and a hydrophobic semipermeable membrane with hydrophilic pores, formed of an expanded polytetrafluroethylene material. This material is normally hydrophobic and its pores are made hydrophilic by treatment with a surfactant.

Again in general, a process according to the present invention includes the separating of analyte components from particulate and/or cellular components using a matrix of pliable hydrophobic interconnecting fibrils which are sufficiently thin to allow the passage of the analyte with the material functioning to keep particulate and/or cellular components from passing through when the material has been treated with a surfactant. The process includes the subsequent step of removing the matrix so that the particle free analyte can be processed or a reaction caused by it can be directly viewed.

Still further in general and in one form of the invention a disposable blood component level measuring arrangement has a blood plasma component reactive area and an overlay which is permeable by the blood plasma or serum components and impermeable by blood cellular components. The overlay is superposed over the reactive area to receive a blood sample and subsequently separable therefrom to expose the reactive area for visual inspection. The overlay is formed of a hydrophobic material which has been treated with a surfactant to make its pores hydrophilic and a further overlay also surfactant treated may be employed to more uniformly distribute the blood sample to the reactive area.

BRIEF DESCRIPTION OF THE DRAWINGS

FIG. 2 is an exploded edge view of a test strip manufactured in accordance with the techniques of the present invention;

FIG. 3 is a plan view of partially completed test strips in accordance with the present invention;

FIG. 4 is a plan view of a completed test strip;

FIG. 5 is a view in cross-section along lines 5—5 of FIG. 3;

FIGS. 6a through 6e illustrate in exaggerated form a portion of a test strip and migration of a blood sample therein;

FIG. 7 is a perspective view of the test strip of FIG. 4 during use; and

FIG. 8 is a view similar to FIG. 7 but illustrating a multiple component test strip in use.

Corresponding reference characters indicate corresponding parts throughout the several views of the drawings.

Figure 1:
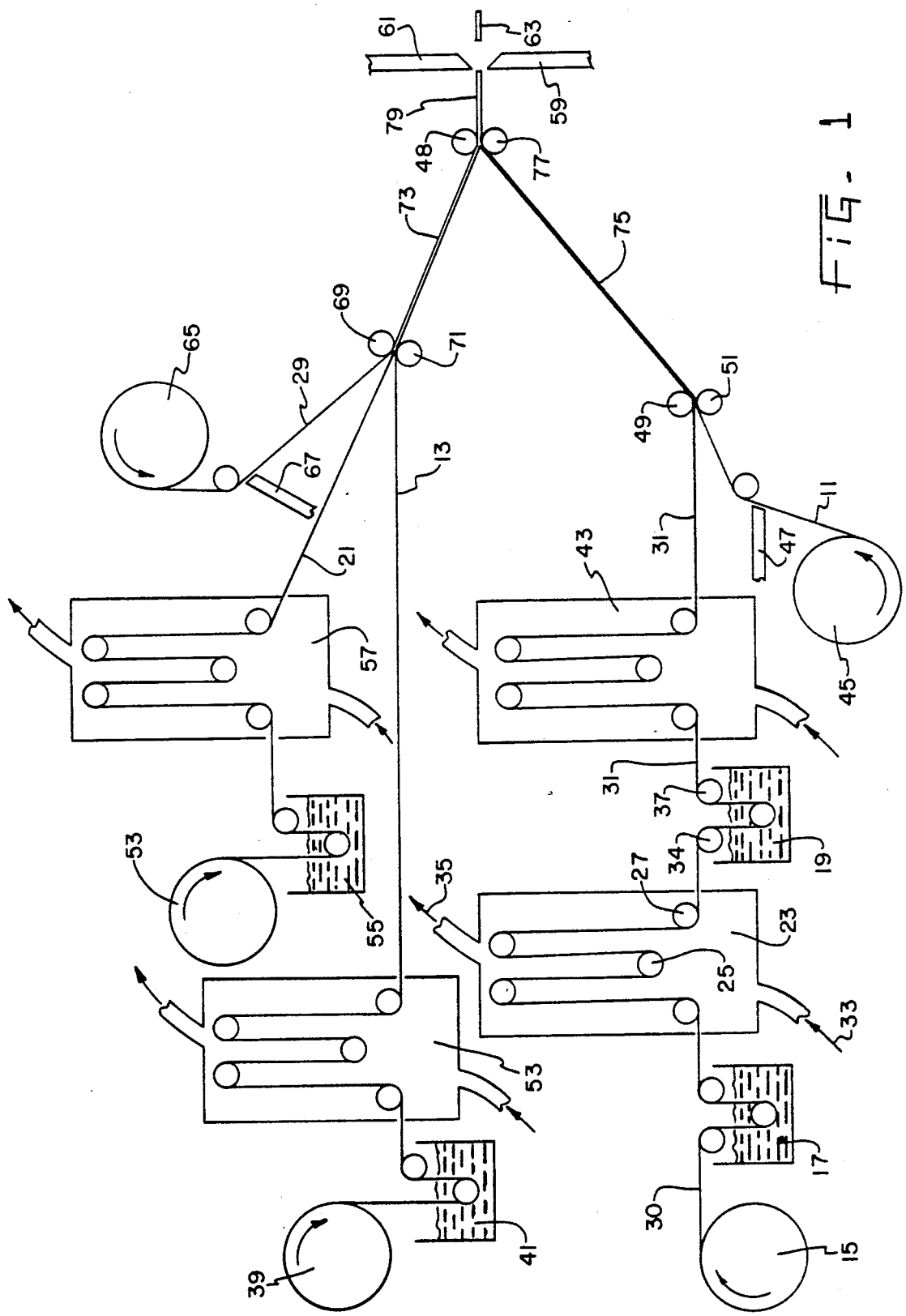
FIG. 1 is a simplified partially schematic view of apparatus for fabricating test strips in accordance with the present invention.

The exemplifications set forth herein illustrate a preferred embodiment of the invention in one form thereof and such exemplifications are not to be construed as limiting the scope of the disclosure or the scope of the invention in any manner.

BRIEF DESCRIPTION OF THE PREFERRED EMBODIMENT

Referring briefly to FIGS. 2 and 7, the product which is the object of the manufacturing portion of the present invention has a carrier matrix 30 (FIG. 1) impregnated with a composition of matter thereby forming a reactive pad 31 for performing the desired testing function. Reactive pad 31 is bonded to a support strip 11 such as a polyester or other paper or plastic material which is inert as far as any reactions are concerned and functions simply as a means for manipulating the reactive pad 31. Strip 11 may for example be on the order of 3 inches in length and 3/16ths of an inch in width and of any convenient thickness such as five to ten thousandths of an inch. The carrier matrix 30 forming the reactive pad may be of any of a wide variety of materials as, for example, suggested in the aforementioned U.S. Pat. No. 4,362,697. Simple chemical filter paper has been successfully used. The reactive pad 31 is covered by a semipermeable membrane 13 and by a further overlay 21 with the overlay 21 and semipermeable membrane 13 being stripped off or torn away during use of the test stick.

The reactive pad 31 and strip 11 are fabricated somewhat in accordance with the aforementioned U.S. application Ser. No. 703,335 (U.S. Pat. No. 4,786,596) as depicted in the lower portion of FIG. 1. A roll source of filter paper 30 is illustrated at 15 and will ultimately be the source of the reactive pads 31. A two stage dipping process at 17 and 19 is employed to appropriately impregnate the carrier matrix or filter paper. However, this impregnation may in some cases be accomplished by a single dipping step. The strip of filter paper is passed through the bath or dip 17 to impregnate the filter paper with certain of the components of the present inventive composition of matter and subsequent to that dipping the filter paper strip is dried at 23 by a steam of hot air. For example, the strip may pass over a series of driven and idle rollers such as 25 and 27 so as to execute a lengthy circuitous path through a comparatively tall oven through which hot air is passed as indicated by the arrows 33 and 35. Thereafter the strip passes around further rollers such as 34 and 37 and through a second dip process 19 to absorb additional composition of matter components. The strip is then subjected to a second tunnel drying operation 43, similar to 23 at the output of which the strip now carries in a dry state all of the components required of the reactive pad. This dried pad is now adhered to the support strip by a pair of pinch rollers 49 and 51. For example, the support material may come from roll 45 and receive an adhesive coating at 47 preparatory to being squeezed with the reactive pad by the pinch rollers. Mounting of the reactive pad on the polyester backing or strip may also be accomplished employing a transfer tape and generally speaking other than the constituents of the dips 17 and 19, the process as thus far discussed in conjunction with FIG. 1 parallels that disclosed in the aforementioned co-pending application Ser. No. 703,335 (U.S. Pat. No. 4,786,596). The first overlay 13 of FIGS. 2, 6 and 7 is a semipermeable membrane to be superposed over the blood plasma component reactive area 31. This semipermeable membrane may for example be of a naturally hydrophobic material treated to make the pores hydrophilic by a surfactant. An expanded polytetrafluoroethylene material such as Gore-Tex, available from W. L. Gore and Associates of Alkton, Md. and having pore sizes ranging from 0.2 to 15 microns has been found suitable. A reel supply of this semipermeable membrane material 39 is in FIG 1 fed through a dip 41 of a surfactant or soap-like material which functions generally as a wetting agent to convert the pores of the naturally hydrophobic material to hydrophilic ones. Subsequent to the dip 41, strip 13 may be air dried or passed through a tunnel dryer 53, similar to dryer 23.

A further overlay 21 which is a polyester, cellulose or similar material sheet and which functions to distribute or spread and meter a blood sample is supplied from roll 53 and passed through a surfactant bath 55 and then air dried or dried in a still further tunnel dryer 57. A final coversheet 29, which like the base or support sheet 11 is primarily for manipulative purposes, is supplied from roll 65 past a wick-like adhesive applicator 67 similar to wick 47 and the strips 29, 21 and 13 joined by pinch rollers 69 and 71. The composite sheets 73 and 75 are further joined passing through pinch rollers 48 and 77 providing the overall composite ribbon at 79 in the form depicted in FIG. 3. Subsequent cutters 61 and 59 sever sheet 79 into individual test strips 63, for example as illustrated in FIGS. 4 and 7. Such severing by the cutters 59 and 61 of course occurs along dotted lines such as 81 and 83 in FIG. 3. Also preferably an edge of strip 29 is folded under as illustrated at 85 to facilitate a user subsequently removing strip 29 and those overlays adhering thereto. Strip 29 may be double stranded or otherwise perforated so as to also provide a tip strip 87 which may be desirable in some versions of the present invention.

The process of testing whole blood to determine the concentration of certain plasma components thereof is illustrated in FIGS. 6, 7 and 8. The superposed semipermeable membrane 13 and blood plasma component reactive area 31 are subjected to a whole blood sample in the form of blood drop 89 applied thereto as in FIG. 6a. Overlay 21, having been treated by a surfactant in bath 55 absorbs and distributes blood sample 89 so that the sample rapidly spreads throughout the width and length of the overlay above the reactive area 31 very rapidly, as illustrated in FIGS. 6a and 6b. As the sample reaches semipermeable membrane 13, plasma components 90 of the sample pass through the semipermeable membrane 13 while that membrane blocks the cellular and particulate blood components. Thus, plasma is uniformly presented to the reactive area 31 as illustrated in the transition between FIGS. 6b 6c. After a specified time interval, the user grasps support sheet 11 and the folded over tab 85 tearing the component level determination stick apart, as illustrated in FIGS. 6d, 7 and 8, removing semipermeable membrane 13 and the cellular and particulate blood components trapped thereby and clearly exposing the reactive area 31 for visual inspection such as color comparison to a standardized color chart. Any of several other colorimetry techniques such as use of a densitometer or reflectometer may also be employed.

EXAMPLES

The following examples illustrate suitable components which may be employed generally in accordance with the apparatus illustrated in FIG. 1 or in some cases in a somewhat more simplistic manner to provide the test strips and accomplish the blood plasma component testing as heretofore described. Peroxidase and other suitable peroxidatively active substances as well as the indicators employed in some of these examples are more completely described in U.S. Pat. No. 4,361,648 as well as the aforementioned co-pending application.

Many of the surfactants in the following examples are identified by trademark. The corresponding generic terminology is as follows:

| TRADE-MARK | GENERIC NAME |
|---|---|
| Triton X-45 | Isooctyl phenyl poly(5)ethoxy ethanol |
| Triton X-100 | Isooctyl phenyl poly(9-10)ethoxy ethanol |
| Triton X-67 | Alkyl polyether alcohol |
| Tween 80 | Polysorbate 80 |
| Brij 35 | Polyoxyethylene 23-Lauryl Ether |
| Igepal CO-630 | Nonyl phenoxy poly(9)ethyleneoxy ethanol |
| Igepal CO-710 | Nonyl phenoxy poly(10-11)ethyleneoxy ethanol |
| Emulphogene DA-630 | Decyloxy poly(6)ethyleneoxy ethanol |
| Antarox BL-236 | modified linear aliphatic polyether |
| Renex 698 | Nonyl phenoxy poly(9)ethyleneoxy ethanol |
| Tergitol 4 | Sodium tetradecyl sulfate |
| Gafac RA-600 | aliphatic polyethyleneoxy phosphate ester |
| Gafac RE-610 | aliphatic polyethyleneoxy phosphate ester |
| Hyamine 1622 | Para diisobutyl phenoxy ethoxy ethyl dimethyl benzylammonium chloride |
| Zonyl FSK | Poly(3-8)tetrafluoroethylene isoproplacetate dimethylammonium acetic acid |
| Zonyl FSN | Poly(3-8)tetrafluoroethylene polyethylene oxide ethanol |
| Zonyl FSO | Poly(3-8)tetrafluoroethylene polyethylene oxide ethanol |
| Zonyl UR | Mono and dibasic polytetrafluoroethylene ethyl phosphate. |

EXAMPLE I

EXAMPLE I

| A. First Dip Mix 17 | |
|---|---|
| Algin | 100 mg in 4 ml H$_2$O |
| Glucose Oxidase (126 U/mg) | 8 mg in 1 ml H$_2$O |
| Peroxidase (114 U/mg) | 4 mg in 1 ml H$_2$O |
| Gelatin (100 mg/ml) | 2 ml |
| Buffer (1M, pH 4.8 citrate) | 10 ml |
| Triton X-100 (1%) | 2 ml |

Filter paper strips were impregnated with the above and dried in a tunnel dryer.

| B. Second Dip Mix 19 | |
|---|---|
| Tetramethylbenzidine | 400 mg in 20 ml xylene |

The impregnated filter strips were immersed in the second dip mix and dried in a tunnel dryer. The strips were mounted on a polyester backing with a transfer tape.

C. Preparation of Membrane 13

A 3 micron pore size expanded Polytetrafluoroethylene (PTFE) membrane (Gore-Tex) was dipped into a 1% Triton X-67 in isopropyl alcohol and air dried.

D. Preparation of Overlay 21

A polyester sheet such as Hollytex 3257 or a celulose acetate sheet such as a Celanese development product or cellulose sheet such as Kimwipes was dipped into the 1% Triton X-67 and air dried.

E. Assembly of Stick

The assembly of the blood glucose stick is shown in FIG. 2.

F. Use of Stick

A drop of blood is placed on the overlay shown in FIG. 6A. The blood rapidly spreads throughout the overlay 21. The glucose, water and other components from the blood are transferred through the membrane 13 to the reactive pad 31. At a suitable time, such as 1 or 2 minutes, the membrane and overlay are stripped off, carrying the blood stain away and leaving a blue color proportional to the blood glucose level on the pad.

EXAMPLE II

Same as Example I, but omitting the overlay. The blood is placed directly on the membrane.

EXAMPLE III

Same as Example I, but the overlay is not treated with surfactant.

EXAMPLE IV

Same as Example I, but the surfactant is 5% Triton X-67 in isopropyl alcohol.

EXAMPLE V

Same as Example I, but the surfactant may range up to 50%.

EXAMPLE VI

Same as any of Examples I–V, except the surfactant may be Tween 80, Brij 35, Igepal CO-630, Igepal CO-710, Emulphogene DA-630, Antarox BL-236, Renex 698, Triton X-100, Triton

EXAMPLE VII

Same as any of Examples I–V, except the surfactant may be lauryl sulfates, Tergitol, 4 GAFAC RA-600, GAFAC RE-610, soap, or any other anionic surfactant.

EXAMPLE VIII

Same as any of Examples I–V, except the surfactant may be a cationic one, such as Hyamine 1622.

EXAMPLE IX

Same as Examples I–V, except the surfactant may be an amphoteric one such as Zonyl FSK.

EXAMPLE X

Same as Examples I–V, except the surfactant may be chosen from the fluorosurfactants known as ZONYL FSN, FSK, PSO, and UR.

EXAMPLE XI

| A. First Dip Mix 17 | |
| --- | --- |
| Algin | 1000 mg in 40 ml $H_2O$ |
| Alcohol oxidase | 10,000 units in 16 ml $H_2O$ |
| Peroxidase (188 U/mg) | 214 mg in 10 ml $H_2O$ |
| $H_2O$ | 14 ml |
| Gelatin (100 mg/ml) | 20 ml |
| Buffer (Tris-malonate) 1M, pH 7.2) | 100 ml. |

Filter paper strips were impregnated with the mix and dried in a tunnel dryer.

| B. Second Dip Mix 19 | |
| --- | --- |
| Tetramethylbenzidine | 4000 mg in 200 ml xylene |

The impregnated strips were dipped in this mix and dried in the tunnel dryer. The strips were mounted on polyester backing with transfer tape.

C. Preparation of Membrane 13 as in Example I.
D. Preparation of overlay 21 as in Example I.
E. Assembly of sticks as in Example I.
F. Use of stick.

As in Example I, except this stick measures blood alcohol.

EXAMPLES XII–XX

Same as Examples II–X using the alcohol stick of Example XI.

EXAMPLE XXI

| A. First Dip Mix 17 | |
| --- | --- |
| Algin | 10 mg in .4 ml $H_2O$ |
| Cholesterol oxidase (18.6 U/mg) | 4.8 mg in .2 ml $H_2O$ |
| Cholesterol esterase (90 U/mg) | 2 mg in .2 ml $H_2O$ |
| Peroxidase (114 U/mg) | 2 mg in .1 ml $H_2O$ |
| Gelatin (100 mg/ml) | .2 ml |
| Buffer (1M, pH 7.5 Tris malonate) | 1 ml |

Filter paper strips were impregnated and dried.

| B. Second Dip Mix 19 | |
| --- | --- |
| Tetramethylbenzidine | 40 mg in 2 ml xylene |

The impregnated strips were dipped into the mix and dried in a tunnel dryer.

C. Preparation of membrane 13 as in Example I.
D. Preparation of overlay 21 as in Example I.
E. Assembly of stick as in Example I.
F. Use of stick A drop of blood is placed on the overlay. After 2 minutes, the overlay together with the membrane is stripped off leaving a blue color proportional to the total cholesterol level of the blood.

EXAMPLES XII–XXX

Same as Examples II–X using the Cholesterol stick of Example XXI.

EXAMPLE XXXI

| Urease | 1000 units in 25 ml $H_2O$ |
| --- | --- |
| Algin | 500 mg in 2 ml $H_2O$ |
| Pnenol Red | 100 mg in 23 ml $H_2O$ |
| Buffer (.2M pH 5 Citrate) | 50 ml |

Strips are dipped in the mix and dried in a tunnel dryer. The membranes of the previous examples are applied. When a drop of blood is placed on the stick, a yellow to orange to red color develops proportional to the urea level of the blood.

EXAMPLE XXXII–XL

Same as Examples II–X using the blood urea stick of Example XXXI.

EXAMPLE XLI

| Uric Acid Determination | |
| --- | --- |
| A. First Dip Mix | |
| Algin | 100 mg in 4 ml $H_2O$ |
| Uricase | 800 units in 1 ml $H_2O$ |
| Peroxidase (114 U/mg) | 4 mg in 1 ml $H_2O$ |
| Gelatin (100 mg/ml) | 1 ml |
| Buffer (1M, pH 7 Phosphate) | 10 ml |
| Triton X-100 (1%) | 2 ml |

Filter paper strips were impregnated and dried.
B. Second Dip Mix as in Example I.

C. Membrane preparation as in Example I.
D. Overlay as in Example I.
E. Assembly as in Example I.

EXAMPLES XLII–L

Same as Examples II–X using the Uric Acid stick of Example XLI.

EXAMPLE LI

A calcium ion detection pad is prepared from the calcium indicator, o-cresolphthalein complexone, a buffer of pH 10–12 and 8-hydroxyquinoline. The pad is covered with the treated membrane and overlay of the previously described examples.

EXAMPLE LII

A. An unimpregnated filter paper backed with an adhesive transfer tape was mounted on a polyester backing.
B. Preparation of membrane as in Example I(C).
C. Preparation of overlay as in Example I(D).
D. The assembly of the stick is shown in FIG. 2.
E. Use of Stick.

A drop of blood is placed on the overlay shown in FIG. 6A. The blood rapidly spreads throughout the overlay 21. The glucose, water and other components from the blood are transferred through the membrane 13 to the unreactive pad 31. At a suitable time, such as to the unreactive pad 31. At a suitable time, such as 2 to 3 minutes, the membrane and overlay are stripped off, carrying the blood stain away and leaving the transferred components in this pad. The pad end of the stick was immersed in a Trinder reagent for measuring glucose. The stick and reagent were incubated for 20 minutes. This reagent was read spectrophotometrically at 505 nm against a blank reagent, and the difference in absorbance proportional to the blood glucose level was noted.

EXAMPLE LIII

Same as Example X, but a surfactant of 1% ZONYL FSN in isopropyl alcohol is applied to the filter paper pad.

EXAMPLE LIV

A. A tablet was made by mixing plaster of Paris and water to form a working paste. The paste was applied to a polyester backing strip and allowed to air dry at room temperature.
B. Preparation of membrane as in Example I(C).
C. Preparation of overlay as in Example I(D).
D. The assembly of the stick is shown in FIG. 2 with the dried plaster of Paris tablet taking the place of the reactive pad 31.
F. Use of Stick A drop of blood is placed on the overlay shown in FIG. 6A. The blood rapidly spreads throughout the overlay 21. The glucose, water, and other components from the blood are transferred through the membrane 13 to the unreactive tablet. At a suitable time, such as 2 to 3 minutes, the membrane and overlay are stripped off, carrying the blood stain away and leaving the transferred components in the tablet.

The tablet end of the stick was immersed in a Trinder Reagent for measuring glucose and stirred until the tablet was dissolved. The reagent was incubated at room temperature for twenty minutes, allowing the plaster of Paris to precipitate and the reaction to go to completion. The clear reagent was read spectrophotometrically at 505 nm against a blank reagent and the difference in absorbance proportional to the blood glucose level was noted.

EXAMPLE LV

Treated filter paper 8/16×3/16
Glucose - Mfg. same as Example XXXI
Alcohol - Mfg. same as Example XI (A & B)
Uric Acid
Calcium
Cholesterol - Mfg. same as Example XXI (A & B)
Transfer tape
Polyester backing
Gore-Tex 5/16×5/16 5 micron membrane wetted with Triton
X-67 (1% in isopropyl alcohol) and dried
¼"×¼" replaceable label stock with a centered 3/16"×
3/16" cutout
5/16"×5/16" spun polyeter wetted with Triton X-67 (1% in
isopropyl alcohol) and dried The dried overlay attached to label stock to form a window.

The membrane element was applied so the membrane window was over each pad. After each pad was covered the overlay element was also put so that the overlay window was over the pad. A tab was then attached so the two (2) elements could be pulled from the polyester backing and the reactive pad. Whole blood was applied to each pad overlay and two (2) minutes were allowed to elapse and the two (2) element assembly was removed by use of the tab. Color development in relation to concentration of analyte was observed on each pad.

The foregoing examples illustrate techniques for forming a blood component level determination stick having a supporting strip 11, a reactive pad 31 and a hydrophobic semi-permeable membrane 13 with hydrophilic pores formed, for example, of an expanded polytetrafluoroethylene material and suitable for testing for a wide variety of blood plasma components. A single disposable blood component level measuring arrangement may, as illustrated in FIG. 8, be employed to test for more than one plasma component at a time. In FIG. 8, the supporting strip 11 has a reactive pad 31 treated in accordance with one of the foregoing examples while reactive pad 91 is treated in accordance with a different one of the foregoing examples, thus giving rise to a disposable blood component level measuring arrangement wherein the reactive area comprises a plurality of discrete subareas each having a different chemical composition and reacting with different blood plasma components. The overlay 13 in FIG. 8 is as heretofore described impermeable by blood cellular components and superposed over the reactive area initially to receive a blood sample and subsequently separable therefrom to expose the several reactive subareas 31 and 91 for inspection.

From the foregoing it is now apparent that a novel test strip fabrication and use technique as well as a unique composition of matter suitable for use in such techniques have been disclosed meeting the objects and advantageous features set out hereinbefore as well as others and that modifications as to precise configuration, shapes, components and details may be made by those having ordinary skill in the art without departing from the spirit of the invention or the scope thereof as set out by the claims which follow.

What is claimed is:

1. A blood component level determination stick comprising a supporting strip, a reactive pad disposed on the supporting strip, and a hydrophobic semipermeable membrane with hydrophilic pores formed of an expanded polytetrafluoroethylene material superposed over the reactive pad.

2. The stick of claim 1 further including an absorbent overlay for receiving, spreading, and metering an applied blood sample to the semipermeable membrane.

3. The stick of claim 1 wherein the reactive pad contains an enzyme for catalyzing a reaction converting a selected blood component and generating hydrogen peroxide as a result of that conversion, a peroxidatively active material, and an indicator material which is oxidized by hydrogen peroxide in the presence of the peroxidatively active material providing a component indicative color change in the indicator material.

4. The stick of claim 1 wherein the reactive pad contains glucose oxidase, peroxidase, and an indicator material.

5. The stick of claim 1 wherein the reactive pad contains cholesterol oxidase, cholesterol esterase, peroxidase, and an indicator material.

6. The stick of claim 1 wherein the reactive pad contains uricase, peroxidase, and an indicator material.

7. The stick of claim 1 wherein the reactive pad contains alcohol oxidase, peroxidase and an indicator material.

8. The stick of claim 1 wherein the reactive pad contains urease, and a pH indicator material.

9. A disposable blood component level measuring arrangement comprising a blood plasma component reactive area, and an overlay formed of a hydrophobic expanded polytetrafluoroethylene containing material which has been treated with a surfactant to make the pores hydrophilic, the overlay being permeable by blood plasma components and impermeable by blood cellular components, the overlay being superposed over the reactive layer to receive a blood sample and subsequently separable therefrom to expose the reactive area for inspection.

10. The measuring arrangement of claim 9 wherein the material is particle size discriminatory having pore sizes ranging from 0.2 to 15 microns.

11. The measuring arrangement of claim 9 wherein the reactive area comprises a plurality of discrete subareas, each having a chemical composition different from the others and reacting with different blood plasma components.

12. A blood cholesterol level determination stick comprising a supporting strip, a reactive pad containing cholesterol oxidase, cholesterol esterase, peroxidase and an indicator material disposed on the supporting strip; and a semipermeable membrane formed of an expanded porous hydrophobic material which has been treated with a surfactant to make the material hydrophilic superposed over the reactive pad.

* * * * *